United States Patent
Marques et al.

(10) Patent No.: US 9,980,998 B2
(45) Date of Patent: May 29, 2018

(54) MEDICINAL COMPOSITION HAVING ANTIBIOTIC, ANTI-INFLAMMATORY, AND WOUND HEALING ACTIVITY

(71) Applicants: Douglas Spalato Marques, Tatui/SP (BR); Marcos Spalato Marques, Sorocaba/SP (BR)

(72) Inventors: Douglas Spalato Marques, Tatui/SP (BR); Marcos Spalato Marques, Sorocaba/SP (BR)

(73) Assignee: BRAERG—GRUPO BARŚILEIRO DE PESQUISAS ESPECIALIZADAS LTDA., Sorocoba (BR)

( * ) Notice: Subject to any disclaimer, the term of this patent is extended or adjusted under 35 U.S.C. 154(b) by 356 days.

(21) Appl. No.: 14/877,654

(22) Filed: Oct. 7, 2015

(65) Prior Publication Data
US 2017/0100443 A1    Apr. 13, 2017

(51) Int. Cl.
| | | |
|---|---|---|
| A61K 36/28 | (2006.01) |
| A61K 36/61 | (2006.01) |
| A61K 36/68 | (2006.01) |
| A61K 36/76 | (2006.01) |
| A61K 9/70 | (2006.01) |

(52) U.S. Cl.
CPC ............ *A61K 36/28* (2013.01); *A61K 9/7007* (2013.01); *A61K 36/61* (2013.01); *A61K 36/68* (2013.01); *A61K 36/76* (2013.01)

(58) Field of Classification Search
CPC ......... A61K 36/28; A61K 36/61; A61K 36/68
USPC ....................................................... 424/738
See application file for complete search history.

(56) References Cited

U.S. PATENT DOCUMENTS

| | | | | |
|---|---|---|---|---|
| 7,678,768 B2* | 3/2010 | Purpura | ............... | A61K 31/353 424/774 |
| 8,491,941 B1* | 7/2013 | Langley | ................. | A61K 36/28 424/725 |
| 8,580,317 B2* | 11/2013 | Waugh | ................. | A61K 31/192 424/725 |
| 2004/0071757 A1* | 4/2004 | Rolf | ....................... | A61K 9/007 424/443 |
| 2009/0252796 A1* | 10/2009 | Mazed | ................... | A61K 36/02 424/484 |
| 2010/0021571 A1* | 1/2010 | Waugh | ................. | A61K 31/192 424/747 |
| 2011/0311661 A1* | 12/2011 | Behr | ...................... | A61Q 17/04 424/750 |
| 2017/0087199 A1* | 3/2017 | Patron | ................... | A61K 36/81 |

\* cited by examiner

*Primary Examiner* — Chris R Tate
(74) *Attorney, Agent, or Firm* — Fitch, Even, Tabin & Flannery, LLP

(57) ABSTRACT

A medicinal composition having antibiotic, anti-inflammatory, and wound healing activity that inhibits the growth of pathogens by means of a synergistic association of plant extracts of *Matricaria recutita*, *Psidium guajava* L., and *Plantago major* L., and, optionally, *Casearia sylvestris* SW, for topical application either in the form of biofilm or in the solid dosage form without the use of preservatives is described.

9 Claims, 2 Drawing Sheets

MEDICINAL COMPOSITION HAVING ANTIBIOTIC, ANTI-INFLAMMATORY, AND WOUND HEALING ACTIVITY

FIELD

A medicinal composition having antibiotic, anti-inflammatory, and wound healing activity, and in particular, a medicinal composition that inhibits the growth of pathogens by means of a synergistic and unexpected association of plant extracts of *Matricaria recutita*, *Psidium guajava* L., and *Plantago major* L., and, optionally, *Casearia sylvestris* SW, said formulation being intended for topical application or in the form of a biofilm or solid dosage form without the use of preservatives.

BACKGROUND

Wound healing is a complex and orderly phenomenon that involves several processes, including regeneration, migration, and proliferation of parenchymal and connective tissue cells, synthesis of proteins of the extracellular matrix (ECM), remodeling of the connective tissue, parenchymal components, collagenization, and acquisition of wound strength (KEDE, M. P. V.; SABATOVICH, O. Wound Healing. Esthetic Dermatology—Revised and Broadened—2nd edition. EDITORA ATHENEU. Sao Paulo, Rio de Janeiro, Belo Horizonte, 2009, p. 11-16).

The efficiency of tissue repair promotes re-epithelialization of the epidermis and replacement of the dermis by a new extracellular matrix. Thus, the loss of parts that may change tissue architecture leads to a fibroproliferative response, resulting in a palpable and visible fibrous scar. When a trauma is persistent or recurrent, the inflammation is perpetuated and tissue repair is delayed and, as a result, wound healing is deficient or fibrosis is excessive. Soluble mediators, blood elements (extracellular matrix) are involved in tissue repair which is divided into phases identified as inflammation, proliferation, and remodeling (KEDE, M. P. V.; SABATOVICH, O. Wound Healing. Esthetic Dermatology—Revised and Broadened—2nd edition, EDITORA ATHENEU, Sao Paulo, Rio de Janeiro, Belo Horizonte, 2009, p. 11-16.).

In most cases, the wound healing process occurs fast and satisfactorily. The wound healing rate depends on the size and location of a wound, which may be incisional or excisional, and a series of local factors such as growth factors, ischemia, edema, low oxygen tension, regional infection (such as arterial, venous insufficiency, and neuropathy) and systemic infection (inadequate perfusion and metabolic disease), nutritional status, pre-existing conditions, the wearing of clothing, exposure to radiation therapy, drinking and smoking habits. When the evolution of a scar is not normal, it results in chronic wounds and, if said evolution is somehow exaggerated, it may result in a hypertrophic scar or keloid. Degradation of the temporary matrix is as important as its formation, whose inappropriate removal may lead to fibrosis; therefore, several factors can interfere with the wound healing process (KEDE, M. P. V.; SABATOVICH, O. Wound Healing. Esthetic Dermatology—Revised and Broadened—2nd edition, EDITORA ATHENEU, São Paulo, Rio de Janeiro, Belo Horizonte, 2009, p. 11-16.).

As for burns, they may have a variety of causes such as sunlight, exposure to chemical agents (acids, caustic products, flammable liquids), physical agents (heat, cold, electricity, radiation) and also burns caused by certain kinds of animals. It is known that human skin can tolerate temperatures of up to 44° C. without any damage. Different lesions are caused above this level, the degree of lesion being directly related to the exposure temperature and time. (ROSSI L A, FERREIRA E, COSTA ECFB, BERGAMASCO 5 EC, CAMARGO C. Burn prevention: perception of patients and their families. Revista Latino-Americana de Enfermagem. 2003; 11 (1): 36-42), and BOLGIANI; SERRA, 2010. Update on local treatment of burns. Revista Brasileira de Queimaduras. 2010; 9 (2): 38-10 44).

The occurrence of burns on the surface of the human body results in losing or compromising the skin protection barrier, which ends up interfering with the normal microbiota and healthy tissue. Thus, a patient becomes susceptible to local or systemic infections (PRUITT B A, MCMANUS at. The changing epidemiology of infection in burn patients, 1992), (TURRINI RNT. Hospital Infection and mortality. USP. 2002; 36 (2): 177-83, 2002) and (HINRICHSEN SL. DIP: Infectious and parasitic diseases. 1st edition. Rio de Janeiro: Guanabara Koogan; 2005).

In addition to destruction of the epithelial barrier, the presence of degraded proteins and devitalized tissue provides an excellent medium for development and proliferation of microorganisms. Therefore, vascular obstruction by thermal damage to the vessels makes it difficult for antimicrobials and cellular components the immune system to arrive of at the burned area (PRUITT B A, MCMANUS at. The changing epidemiology of infection in burn patients, 1992).

The number and variety of topical wound healing preparations is enormous, most of them being inefficient in or detrimental to wound healing as they are irritant and stimulate the formation of exuberant granulation tissue.

Patent application MX2010013360 discloses pharmaceutical compositions for alleviating or removing hypochromic patches on the skin, post-inflammatory hyperpigmentation, patches caused by UV rays, solar lentigo, freckles, maintaining melasmas and chloasmas, and lightening darkened skin, said compositions comprising between 10% and 50% of *Matricaria recutita* natural extract, preservatives (methylparaben, propylparaben) and synthetic compounds. It does not however disclose a synergistic combination of natural extracts and uses different compounds and synthetic preservatives as it is characterized as a cosmeceutical intended only for application in melanocyte-associated diseases.

Patent application U.S. Pat. No. 5,997,876 discloses a composition for burn treatment, said composition comprising extracts of *Chelidonium majus* (15-25 g), *Plantago major* (15-25 g), *Matricaria chamomilla* (15-25 g), *Achillea millefolium* (15-25 g), *Calendula officinalis* (15-25 g), *Hypericum perforatum* (15-25 g), *Eucalyptus globulus* (15-25 g), *Oleum olivarum* (15-25 g), and *Cera flava* (80-130 g). Said composition has no synthetic preservatives and is an ointment for topical application. However, it does not use a synergetic combination of natural extracts as proposed herein.

Patent application US2009004301 discloses a composition for protecting skin from diseases and dyshidrosis, said composition comprising *Juglans nigra* (9%), *Artemisia absinthium* 9%), *Curcuma longa* (7%), *Allium sativum* or propolis (10%), *Glycyrrhiza glabra* (3%), *Hypericum perforatum* (3%), *Matricaria recutita* (2%), niacin (1%), *Aloe vera* (54%) and synthetic preservatives (2%). The concentration of most of the extracts used may range from 0.5% to 90%. However, it discloses natural extracts from plants different from those proposed herein, in addition to using synthetic compounds and preservatives (probably, methylparaben and propylparaben), and niacin (vitamin B3).

Patent application WO03033007 discloses a topical composition having anti-inflammatory and wound healing effects, which may also be applied to excoriations and skin ulcers, said composition comprising extracts of *Matricaria recutita*, *Althaea officinalis*, *Malva sylvestris*, *Tillia platyphyllos* and *Achillea millefolium*.

Patent application RO126747 discloses a composition of a skin calming and wound healing cream comprising *Achillea millefolium* (1%-7%), *Matricaria chamomilla* (4%-8%), *Tagetes patula* (2%-4%), *Lavandula angustifolia* (0.1%-0.3%), *Calendula officinalis* (3%-12%), olive oil (10%), allantoin (0.1%-0.8%), collagen (0.1%-0.5%), chitosan (0.1%-0.2%), lanolin (0.1%-0.15%), nipagin (0.1%-0.5%), nipasol (0.1%-0.5%), triethanolamine (0.1%-0.5%), and distilled water (Q.S.P. 100%).

Patent application JP2003335623 discloses a composition for treating skin aging and inflammations of skin and its annexes, said composition comprising plant extracts from the family Salicaceae and one or more kinds of antioxidants such as carotenoids, flavonoids, tannins, gallic acid and its salts and esters, tocopherol and its derivatives, superoxide dismutase, thioredoxin, thioredoxin reductase, butyl hydroxytoluene, and butyl hydroxyanisole.

However, the exclusive use of vegetable active raw materials has a synergistic effect because they have a broader range of activity, when different substances produce effects at the same time, while synthetic compounds act specifically on an active site.

Taking into account that herbal medicines are used for prophylactic, curative, palliative or diagnostic purposes, in 1978, the World Health Organization started considering medicinal plants as important tools in Pharmaceutical Care. According to surveys, about 80% of the world population depends on traditional practices in terms of primary health care and 85% of this uses plants and plant-based medicinal preparations, and 67% of the species of medicinal plants in the world comes from the developing countries (ALONSO, Tratado de fitomedicina: bases clinicas y farmacológicas. Buenos Aires: ISIS, 1998. 1039 p.). Therefore, disclosed herein are various embodiments of a medicinal composition having anti-inflammatory and wound healing activity that inhibits the growth of pathogens by means of synergistic association of such plant extracts as *Matricaria recutita*, *Psidiumguajava* L. and *Plantago major* L, and, optionally, *Casearia sylvestris* SW, said plants abounding in the Brazilian flora and being easily adaptable.

SUMMARY

Embodiments may provide a medicinal composition having antibiotic, anti-inflammatory, and wound healing activity that inhibits the growth of pathogens by means of a synergistic association of plant extracts of *Matricaria recutita*, *Psidium guajava* L. *Plantago major* L., and *Casearia sylvestris* SW.

In one approach, a medicinal composition is provided having antibiotic, anti-inflammatory, and wound healing activity comprising between 0.1 and 10.0% of the dry extract of *Matricaria recutita*, between 0.1 and 10.0% of the dry extract of *Psidium guajava* L. and between 0.1 and 10.0% of the dry extract of *Plantago major* L.

In one approach, a medicinal composition is provided having antibiotic, anti-inflammatory, and wound healing activity, and the composition may further comprise between 1.0 and 20.0% of dry extract of *Casearia sylvestris* SW.

In one approach, a medicinal composition is provided having antibiotic, anti-inflammatory, and wound healing activity, and the composition may be impregnated in a microbial cellulose biofilm In one approach, a medicinal composition is provided having antibiotic, anti-inflammatory, and wound healing activity wherein the composition may be in a liquid form and may comprise between 0.1% and 10.0% of the lyophilized extract of *Matricaria recutita*, between 0.1% and 10.0% of the lyophilized extract of *Psidium guajava* L., between 0.1% and 10.0% of the lyophilized extract of *Plantago major* L., between 0.01% and 5.0% of the vitamin C, between 0.5% and 3.0% of a wetting agent, between 0.1% and 1% of an antioxidant agent, and water q.s.p.

In one approach, a medicinal composition is provided having antibiotic, anti-inflammatory, and wound healing activity, and the composition may also comprise between 1.0% and 10.0% of the lyophilized extract of *Casearia sylvestris* SW.

In one approach, a medicinal composition is provided having antibiotic, anti-inflammatory, and wound healing activity, and the composition may further comprise a pH of approximately 6.0.

In one approach, a medicinal composition is provided having antibiotic, anti-inflammatory, and wound healing activity, wherein the composition may be in a solid form and may have between 0.1% and 10% of the lyophilized extract of *Matricaria recutita*, between 0.1% and 10% lyophilized extract *Psidium guajava* L., between 0.1% and 10.0% lyophilized extract *Plantago major* L., between 60.0% a 96.0% of a hardness agent and a sweetener, and water q.s.p.

In one approach, a medicinal composition is provided having antibiotic, anti-inflammatory, and wound healing activity, and the composition may further comprise between 1.0% and 10.0% of the lyophilized extract of *Casearia sylvestris* SW.

Embodiments may provide a medicinal composition having antibiotic, anti-inflammatory, and wound healing activity for topical application in the form of biofilm or in solid and semi-solid dosage forms.

Embodiments may provide a medicinal composition having antibiotic, anti-inflammatory, and wound healing activity that may or may not use preservatives and other synthetic compounds.

DETAILED DESCRIPTION

Figure 1:
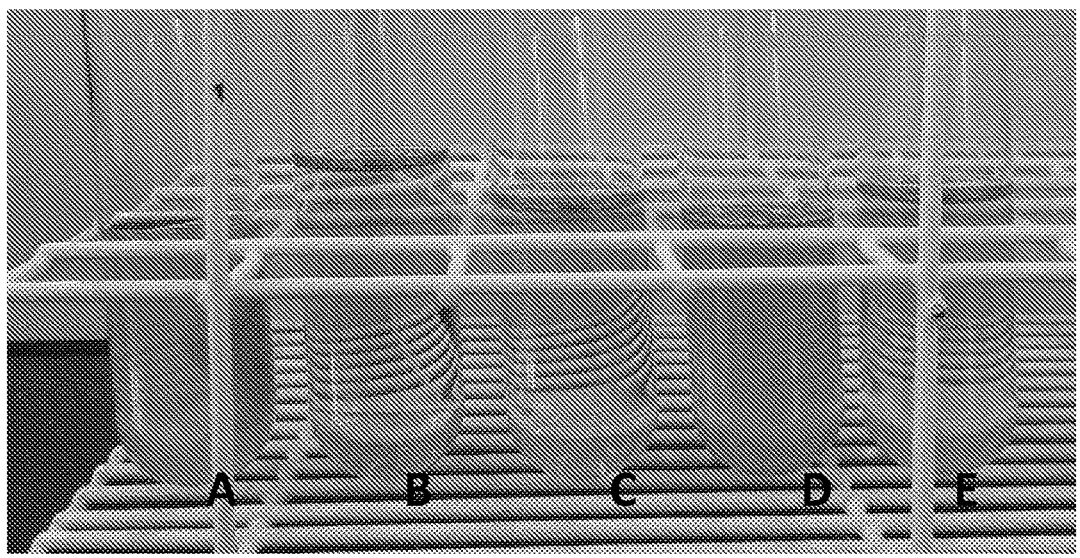
FIG. 1 shows the results of microbial growth in the inoculated media with the respective samples after 24 hours, where (A) is a *Staphylococcus aureus* control, (B)—sterilization control of the broth, (C)—Triclosan @ 0.1%, antimicrobial activity control, (D) candy essay with extracts, and (E) candy essay without extracts.
Figure 2:
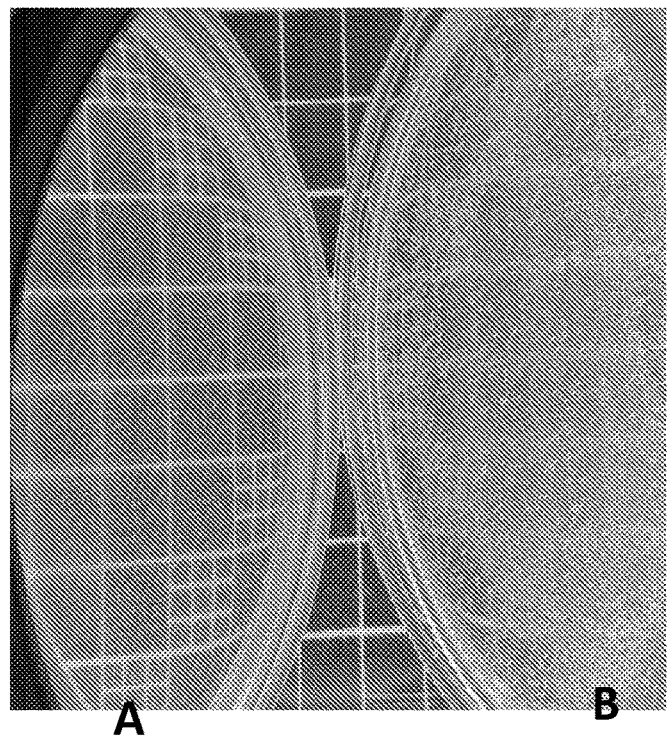
FIG. 2 shows a picture taken in a colony counter of the comparative bacterial growth of 1 mL of the candy samples, demonstrating at the support (A) the aliquot of candies with plant extracts taken after 24 hours of growth, and at the support (B)—the aliquot taken from candies without plant extracts after 24 hours growth.
Figure 3:
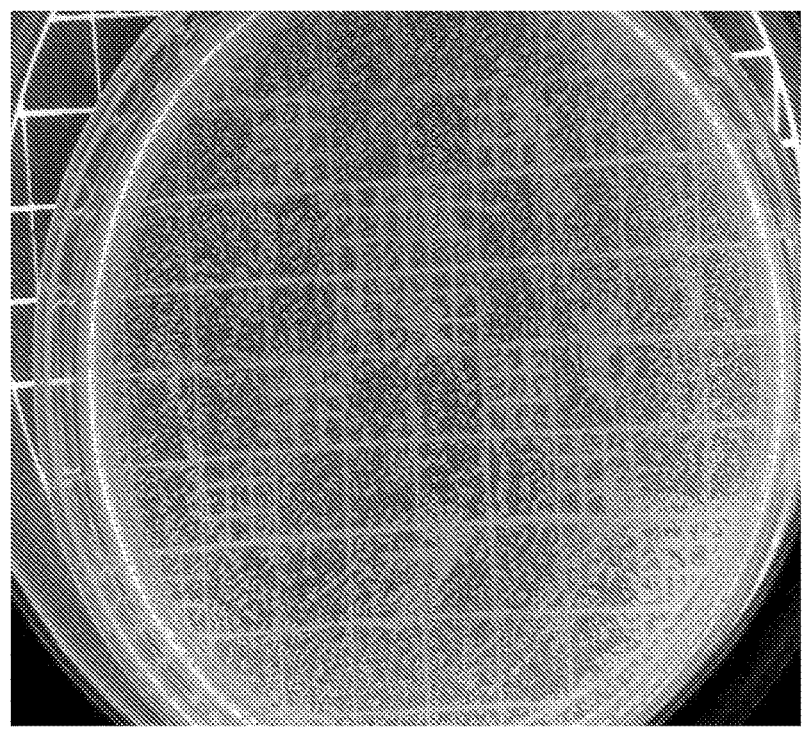
FIG. 3 shows a picture taken in a colony counter of the bacterial growth of 1 mL of the sample of candies without plant extracts, demonstrating at the support the aliquot taken after 24 h essay.
Figure 4:
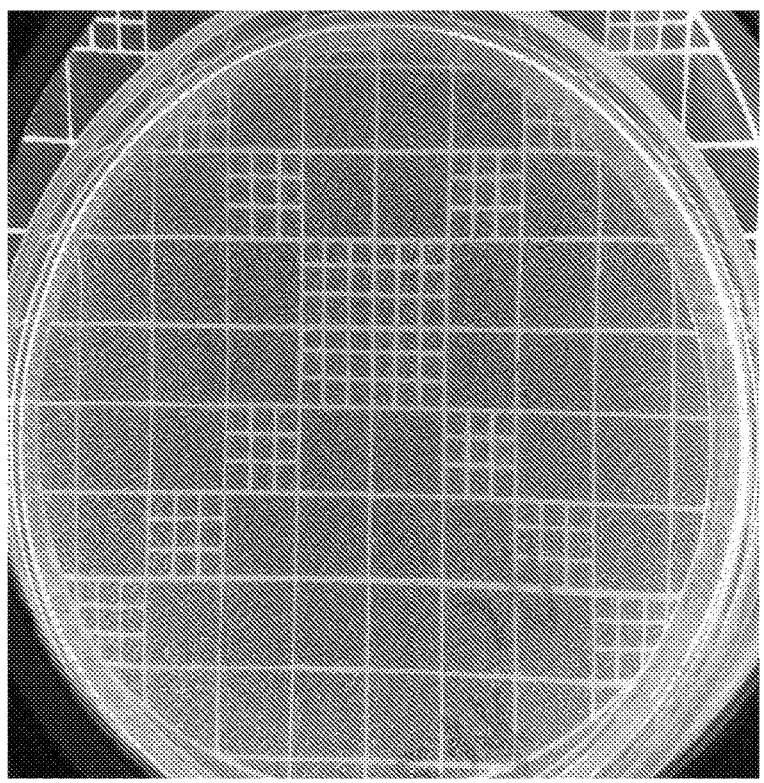
FIG. 4 shows a picture taken in a colony counter of the bacterial growth of 1 mL of the sample of candies with plant extracts, the support being an aliquot taken after 24 h essay.

A medicinal composition having anti-inflammatory and wound healing action comprises a synergistic association of dry plant extracts of *Matricaria recutita* at a concentration of 0.1 to 10.0%, *Psidium guajava* L. between 0.1 and 10.0%, and *Plantago major* L. between 0.1 and 10.0%.

Optionally, it is associated with the formulation comprising between 0.1 and 20.0% of dry extract of *Casearia sylvestris* SW.

*Casearia sylvestris* SW from the family Saliceceae, described in the 1929 Brazilian Pharmacopoeia, is a vegetable species from the tropical and subtropical regions of the Americas and very common in most of the Brazilian states. It is found in all kinds of forest formations and that is why it demonstrates an excellent capacity for genetic adaptation, thus being able to survive in a variety of environments (ALMEIDA, K. C.; BARBOSA, T. R.; SILVA, R. N. R.; JACQUES, D. S.; FREIRE, R. B.; Cytotoxic effect of the water infusion of *Psidiumguajava* L. (Myrtaceae). Revista Brasileira de Farmácia. v. 87, n. 2, p. 60-62, 2006.). As these plants present a great diversity and are found in different places, they have different common names. In Brazil different species are called Guaçatonga, Porangaba and Chá de Bugre (PIO CORRÊA, M. 1984. Dictionary of useful plants of Brazil and exotic crops. Instituto de Desenvolvimento Florestal, Rio de Janeiro, v. 3). They are used in popular medicine due to their antiseptic, antiviral, antiulcer, anticancerous, and wound healing properties.

*Casearia sylvestris* SW is mainly used to treat ulcers, tumors, gastritis, snakebites, and also as a wound healer and antipyretic (PIO CORRÊA, M. 1984. Dictionary of useful plants of Brazil and exotic crops. Brasília: Ministry of Agriculture—IBDF, 1975. p. 514-516). The extracts of its leaves have anti-inflammatory, antiulcerogenic, antineoplastic, wound healing, and antiophidic activity (BASILE, 5 A. C., et al., Pharmacological assessment of *Casearia sylvestris* SW I: Preventive antiulcer activity and toxicity of the crude leaf extract a. J. Ethnopharmacol; v. 30 n 2 p. 185-197, 1990).

*Matricaria recutita* is popularly known as chamomile. It is native to South Africa, but nowadays it can be found practically all over the world. It is also a medicinal plant that has the largest area under cultivation. It has carminative (gas expulsion), anti-inflammatory, and antispasmodic properties. Its anti-inflammatory and antispasmodic activity is related to the components of essential oil and its lactones while the antispasmodic effects are related to flavonoids (RAMOS, M. B. M.; VIEIRA, M. C.; HEREDIA Z., N. A.; SIQUEIRA, J. M.; ZIMINIANI, M. G. Production of capitula of chamomile as a result of plant populations and chicken manure incorporated to the soil. Horticultura Brasileira, 20 Brasília, v. 22, p. 566-572, 2004).

Flavonoids and some terpenoids present in *Matricaria recutita* as well as bisabolol and chamazelene are compounds responsible for anti-inflammatory, antispasmodic, and smooth muscle relaxant activity, particularly, in the gastrointestinal tract (SATORI, 25 L. R.; FERREIRA, M. S.; PERAZZO, F. F.; MANDALHO, L.; CARVALHO, J. C. T., Anti-inflammatory activity of the *Calendula officinalis* L and *Matricaria recutita* L. phytocomplex. Revista brasileira de farmacognosia. v. 13, p. 17-19, 2003). It has been proven that, when used in the form of an infusion, it has anti-inflammatory, antibacterial, liver stimulating, and even antimycotic activity (PETRONILHO, S. L., Characterization of the sesquiterpenic fraction of chamomile populations. Universidade de Avieiro. 2008). Its activity against *Staphylococcus aureus* was scientifically proven by Silva (SILVA, N. C. C. Comparative study of the antimicrobial activity of extracts and essential oils of medicinal plants and synergism with antimicrobial drugs. 2010. 75f. Thesis (MA in General and Applied Biology)—Institute of Biosciences, Universidade Estadual Paulista, São Paulo).

The principal components contained in *Psidium guajava* L., commonly known as guava, are tannins, flavonoids, essential oils, alcohols, sesquiterpenoids and triterpenoid acids as well as a regular quantity of acids, sugars, and pectins. It has antimicrobial, antimutagenic, hypoglycemic activity, among others (ILHA S. M.; Migliato K. F.; Vellosa J. C. R.; Sacramento L. V. Pietro R. C. L. R.; IsaacV. L. B.; Brunettil. L.; Correa M. A.; Salgado H. R. N.; Phytochemical Study of Guava (*Psidium guajava* L.) having the antioxidant potential for development of phytocosmetic formulations. Revista Brasileira de Farmacognosia. v. 18, n. 3, 2008).

Guava leaves and stems have been reported to contain substances that have an antimicrobial activity against *Staphylococcus* ssp., *Shigella* ssp., *Salmonella* ssp., *Bacillus* ssp., *Clostridium* ssp., *Pseudomonas* ssp. and *Escherichia coli*. It also has activity different genera of fungi, yeast (*candida*), amoebas, and *Plasmodium* ssp. (ALMEIDA, K. C.; BARBOSA, T. R.; SILVA, R. N. R.; JACQUES, D. S.; FREIRE, R. B.; Cytotoxic effect of the water infusion of *Psidium guajava* L. (Myrtaceae). Revista Brasileira de Farmácia. v. 87, n. 2, p. 60-62, 2006).

The genus *Plantago* L comprises plants commonly known as "tansagem", "lingua-de-vaca", etc. Many of the species of this genus have several therapeutic properties and particularly its use for treatment of throat and mouth inflammations (ROCHA, J. F.; ROSA, M. M. T.; FRADE, C. C. M.; DIERSMANN, E. M.; Anatomic and histochemical study of *Plantago major* L. e *plantago australis* Lam leaves. Revista universidade rural, v. 22, n. 1, p. 33-10 41, 2002).

*Plantago major* is an herbaceous plant that grows spontaneously in the temperate or subtropical regions, that is why it is a plant easy to grow in Brazil. It is also commonly used as a gargle infusion for treatment of inflammations and infections in the digestive tract. Its anti-inflammatory action is due to terpens that have an important inhibiting effect on cyclooxygenase (COX-1), and its antibiotic activity is due to its glycoside which inhibits the bacterial growth (FREITAS, A. G.; COSTA, V.; FARIAS, E. T.; LIMA, M. C. A.; SOUSA, I. A.; XIMENES, E. A.; Antistaphylococcal activity of *Plantago major* L. Revista brasileira de farmacognosia, v. 12, supl., p. 64-65, 2002).

In a first embodiment, the medicinal composition having antibiotic, anti-inflammatory, and wound healing activity is impregnated in a bacterial cellulose biofilm.

In some embodiments, the medicinal composition may be impregnated into an *Acetobacter xylinum* cellulose biofilm. To isolate *Acetobacter xylinum* (aerobic, gram-negative, and flagellated bacteria), a liquid culture medium containing ripe macerated seedless grapes, 250 ml of red wine, and 250 ml of wine vinegar is used. Said culture medium was chosen due to *Acetobacter*'s characteristics, which develops in acid media and converts ethanol to acetic acid. Ripe grapes were used as a source of carbohydrates, proteins, and nitrogen; grape seeds were removed because they are rich in tannins capable of precipitating proteins and inhibiting the growth of microorganisms.

After seven days of fermentation, it was possible to observe zooglea on the surface of the medium. A solid culture medium (TSA) was used for streaking and isolating the *Acetobacter xylinum* strain which macroscopically have a rough appearance with amorphous albeit well-defined edges.

After isolation, the strain was transferred to a second liquid culture medium containing 1 L of ripe coconut water, 100 ml of acetic acid, and 20 g of glucose. On day 4, the medium was supplemented with 500 ml of ripe coconut water.

The film was transferred to a sterile Petri dish containing 2 ml of a sodium hypochlorite solution and water from reverse osmosis (1:1) for 30 minutes. At the end of this process, the biofilm was washed in reverse osmosis water successive times until it was clean.

The biofilm was cut into 5 cm×5 cm pieces in a sterile environment and with the help of a sterile blade, thus avoiding possible contamination.

Each biofilm was transferred to Petri dishes and weighed on a semi-analytical balance. After weighing, they were immersed for 48 hours in a container containing 1.6 g of base extract of each of the four plants (*Matricaria recutita*, *Psidium guajava* L. and *Plantago major* L., and, optionally *Casearia sylvestris* SW).

The extracts were steeped in the biofilms which were then placed in a sterile oven for drying at 35° C. for 10 hours.

After drying, they were weighed and transferred to Petri dishes. It was observed that the films were able to impregnate 10 mg of extracts for 48 hours, out of which 2.5 mg were from each of the extracts.

In other embodiments the medicinal composition may be in a liquid form.

The medicinal composition having antibiotic, anti-inflammatory, and wound healing activity in a liquid form may comprise between 0.1% and 10.0% of the lyophilized extract of *Matricaria recutita*, between 0.1% and 10.0% of the lyophilized extract of *Psidium guajava* L., between 0.1% and 10.0% of the lyophilized extract of *Plantago major* L., between 0.01% and 5.0% of vitamin C to increase the collagen synthesis; between 0.5% and 3.0% of a wetting agent, preferably, propylene glycol; between 0.1% and 1.0% of an antioxidant agent, preferably, EDTA, and water q.s.p 100%.

Some embodiments, of the medicinal composition may comprise the association of a lyophilized extract of *Casearia sylvestris* SW at a concentration between 0.1% and 20.0%.

In some embodiments the pH of the medicinal composition having anti-inflammatory and wound healing activity in a liquid form may be close to 6.0.

In some embodiments, the medicinal composition having antibiotic, anti-inflammatory, and wound healing activity may be in a solid form, notably, candies and lozenges, comprises between 0.1% and 10.0% of the lyophilized extract of *Matricaria recutita*, between 0.1% and 10.0% of the lyophilized extract of *Psidium guajava* L., between 0.1% and 10.0% of the lyophilized extract of *Plantago major* L., between 60.0% and 96.0% of a hardness agent and a sweetener, preferably, selected among isomaltitol, maltitol, xilitol or sorbitol, isolated or in association; a flavoring component and water q.s.p.

Optionally, the formulation comprises the association of the lyophilized extract of *Casearia sylvestris* SW between 0.1% and 20.0%.

Tests:

The efficiency of the medicinal composition having antibiotic, anti-inflammatory, and wound healing activity, subject matter hereof, was assessed in the strains of *Staphylococcus aureus*, *Escherichia coli* and *Pseudomona saeruginosa*, chosen because they are major disease causing agents in inpatients and outpatients (MACIEL, C. C. S., CÂNDIDO, H. L. R. F. Hospital Infection: Main Agents and Drugs Administered. VEREDAS FAVIP—Revista Eletrônica de Ciências—v. 3, n. 1—janeiro a junho de 2010).

Petri dishes were prepared with 15 ml of Agar Müeller-Hinton which is most suitable for susceptibility tests in bacteria.

The strains of *Staphylococcus aureus*, *Escherichia coli* and *Pseudomonas aeruginosa* were isolated and suspended in 3 different tubes, each containing 10 ml of 0.9% sterile saline solution and incubated in an oven for microbial growth until the turbidity matching the 0.5 McFarland turbidity standard (equivalent to 1×106 UFC/mL) was reached. A barium sulfate suspension was used as a turbidity standard since its value on the MacFarland scale is 0.5.

Then, each of the 3 plates was seeded with one of the above microorganisms, spreading them smoothly in all five directions in order to cover the entire surface. After seeding, the plates were dried at room temperature.

Before inoculating the strains of *Staphylococcus aureus*, *Escherichia coli* and *Pseudomonas aeruginosa*, the following solutions were prepared:

Solution 1: Lyophilized extract of *Matricaria recutita* (5%), lyophilized extract of *Psidium guajava* L. (5%), lyophilized extract of *Plantago* 10 *major* L. (5%), lyophilized extract of *Casearia sylvestris* SW (20%), and ethanol 70° GL (65%).

Solution 2: Lyophilized extract of *Matricaria recutita* (5%), lyophilized extract of *Psidium guajava* L. (5%), lyophilized extract of *Plantago major* L. (5%), lyophilized extract of *Casearia sylvestris* SW (5%), and ethanol 70° GL (80%).

Solution 3: Lyophilized extract of *Matricaria recutita* (3%), lyophilized extract of *Psidium guajava* L. (3%), lyophilized extract of *Plantago major* L. (3%), lyophilized extract of *Casearia sylvestris* SW (3%), and ethanol 70° GL (88%).

Control: Ethanol 70° GL (100%)

Papers for the antibiogram were soaked into each of the solutions in triplicate, producing 4 papers for each solution, which later were transferred to a sterile oven for drying and evaporation of ethanol 70° GL at 35° C. for 10 hours. After drying, 4 papers were placed onto each plate with the help of sterile tweezers, each being impregnated with one of the different solutions and control.

After adding the papers impregnated with the abovementioned solutions to the antibiogram, the plates were inserted upside down in an oven at 36° C. for 48 hours.

The same experiment was carried out three times in order to produce more reliable results as shown in Tables 1, 2, and 3.

TABLE 1

Diameter of the halos in the first execution of the experiment:

| | Solution 1 | Solution 2 | Solution 3 | Control |
|---|---|---|---|---|
| *Staphylococcus aureus* | 21 mm | 18 mm | 18 mm | 0 mm |
| *Escherichia coli* | 18 mm | 16 mm | 16 mm | 0 mm |
| *Pseudomonas aeruginosa* | 20 mm | 19 mm | 19 mm | 0 mm |

TABLE 2

Diameter of the halos in the second execution of the experiment:

| | Solution 1 | Solution 2 | Solution 3 | Control |
|---|---|---|---|---|
| Staphylococcus aureus | 20 mm | 18 mm | 18 mm | 0 mm |
| Escherichia coli | 19 mm | 15 mm | 16 mm | 0 mm |
| Pseudomonas aeruginosa | 21 mm | 19 mm | 19 mm | 0 mm |

TABLE 3

Diameter of the halos in the third execution of the experiment:

| | Solution 1 | Solution 2 | Solution 3 | Control |
|---|---|---|---|---|
| Staphylococcus aureus | 21 mm | 17 mm | 18 mm | 0 mm |
| Escherichia coli | 16 mm | 16 mm | 16 mm | 0 mm |
| Pseudomonas aeruginosa | 19 mm | 19 mm | 19 mm | 0 mm |

TABLE 4

The mean of the halos in the three executions of the experiment:

| | Solution 1 | Solution 2 | Solution 3 | Control |
|---|---|---|---|---|
| Staphylococcus aureus | 20.6 mm | 17.6 mm | 18 mm | 0 mm |
| Escherichia coli | 18 mm | 15.6 mm | 16 mm | 0 mm |
| Pseudomonas aeruginosa | 20 mm | 19 mm | 19 mm | 0 mm |

As shown in the tables above, it is possible to state that the combinations of the plant extracts showed strong antimicrobial activity against the tested microorganisms and that its concentration may influence the size of the generated inhibition halo.

The control group can show that the antimicrobial activity was really caused by the solutions having different combinations of the plant extracts.

A second study was performed to verify the antimicrobial potential of the synergistic combination of the extracts of *Casearia sylvestris* SW, *Matricaria recutita*, *Psidium guajava* L. and *Plantago major* L. against *Staphylococcus aureus*. This study involved the formulation of a candy prepared with the plant extracts, adopting the method of dilution in a liquid medium where the sample aliquots and controls were inoculated as specified below (triplicate):

A) Samples:

Candy dilution: 50% (m/v) dissolution of a candy (with extracts) in a sterile saline solution, weighing 10 g of the candy and dissolving it in 10 g of sterile saline solution for this purpose.

Essay: In replicating 3 tubes containing 18 mL of soybean casein broth inoculated with the strains of *Staphylococcus aureus*, 2 mL of the candy dissolved at 50% m/m (each 10 mL of broth inoculated with $10^6$ UFC were subjected to contact with 1 g of the candy) were added.

B) Controls:

Candy base: Dilution of the candy mass without extracts: 50% (m/m) dissolution of a candy (without addition of the extracts) in a sterile saline solution, weighing 10 g of the candy mass and dissolving it in 10 g of a sterile saline solution for this purpose.

2 mL of the 50% m/m candy base dilution without the extracts were added to the tubes with 18 mL of the culture medium inoculated with *Staphylococcus aureus* (each 10 mL of broth inoculated with $10^6$ UFC were subjected to contact with 1 g of the candy) were added.

Positive growth inhibition control: a standard commercial mouthwash diluted in an innocuous solvent at a known concentration, whose minimum inhibitory concentration was also known, was used. Thus, a saline solution was prepared under Triclosan® aseptic conditions such that a 0.1% m/v concentration in the final inoculated medium was obtained similarly to that of the sample essay. To this end, 0.100 g of Triclosan® in 10 mL of saline solution was weighed, the mixture being heated in the water bath for 30 minute at 60° C. for dissolution. 2 mL of this solution were added to each tube (n=3) containing 18 mL of the inoculated medium (in order to obtain 0.1% in the inoculated medium).

Negative control (medium control): 2 mL of sterile saline solution were added to 3 tubes containing 18 mL of the culture medium inoculated with *Staphylococcus aureus*.

All the essayed tubes were incubated at 36.5° C. for 72 hours. The growth was observed by taking 1 mL aliquots (12 h, 24 h, 48 h, and 72 h), which later were plated by the in-depth seeding technique in 15 to 20 mL of Agar soybean casein for 12 to 24 hours.

The microbial growths were analyzed comparatively to observe a possible inhibitory effect on the growth of *Staphylococcus aureus*, considering the candy formulation with and without plant extracts.

Due to lack of a protocol already established for this purpose, a method that allows greater contact of the components of the formulation with the microorganism was adopted, a method of dilution in a liquid medium having been selected for this. As the idea was to only verify the inhibition potential, a 10% m/v candy concentration (with and without plant extracts) for the culture medium inoculated with $10^6$ UFC/mL was established, the growth being observed by taking 1 mL aliquots at 0 h, 12 h, 24 h, and 36 h.

As shown in FIG. 1, the lower turbidity is verified in tube D (candy with extracts) after 24 hours, demonstrating that the candy with extracts was able to affect the growth of *Staphylococcus aureus*, the colonies being smaller in size and relative quantity when compared to the aliquots taken from the growth tubes with the candy mass without extracts, showing that the combination of the plant extracts of *Casearia sylvestris* SW, *Matricaria recutita*, *Psidium guajava* L. and *Plantago major* L. is capable of interfering sensitively with the growth of the *Staphylococcus aureus* strains.

Efficiency Test of the Formulations Against the Bacterial Growth

To perform the antibiogram using the developed herbal medicines, four plates containing the Mueller Hinton culture medium were prepared, the culture medium having been previously autoclaved and sterile Petri dishes used to prevent any other microorganism from contaminating the experiment.

To confirm the antimicrobial activity of the herbal medicines, the *Staphylococcus aureus* bacterium was chosen since it is one of the most ancient bacterial symbionts of man present in the most varied infections that affect the organism, albeit having diverse toxins.

The lyophilizate of *Staphylococcus aureus* was resuspended in 10 ml of 0.85%, saline solution, 0.01 ml being used for seeding in accordance with the spread plate method adapted by using the method cited by Hindler et al. (1994).

Antibiogram

In this study, in order to verify the antimicrobial potential of the formulation of the herbal medicines, the sample aliquots and controls were inoculated as specified below (triplicate):

Sample: Inoculated with $10^2$ UFC of *Staphylococcus aureus* and containing 1 ml of the candy base with the 50% (m/m) extracts.

Control: Inoculated with $10^2$ UFC of *Staphylococcus aureus* and containing 1 ml of the candy base without the 50% (m/m) extracts.

The microbiological growth of *Staphylococcus aureus* was greatly affected by the herbal medicines which prevented the colonies from developing correctly and made them reproduce in smaller quantities, proving the antimicrobial activity of the herbal medicines.

The MIC assessment method was performed in a serial dilution where at first 9 ml of the previously autoclaved Mueller Hinton broth were added to 4 sterile tubes; then 1 ml of a solution at a standard concentration of $10^5$ UFC/ml de *Staphylococcus aureus* was added to the first tube which was centrifuged for 10 seconds, 1 ml from this tube being transferred to the second one and the process being repeated twice in order to obtain 4 tubes containing the concentrations of $10^4$, $10^3$, $10^2$ and 10 UFC/ml.

Soon after dilution, 0.8 g of the mixture of the lyophilized extracts was added. The tubes were taken for incubation at 36° C. for 48 hours and, after this period of time, 1 ml was inoculated on the plates containing the Mueller Hinton culture and incubated for 48 hours for each of the 4 tubes, observing the microbiological growth at 12 h, 24 h, and 48 h.

The absence of turbidity of the broths and the absence of UFCs on the plates were observed, demonstrating that the combination of the extracts completely inhibited the microbiological growth in all of the concentrations of microorganisms.

Because other modifications and changes varied to fit particular requirements and environments will be apparent to those skilled in the art, the disclosure is not considered limited to the examples chosen for purposes of illustration, and covers all changes and modifications which do not constitute departures from the true spirit and scope of this disclosure.

We claim:

1. A medicinal composition having antibiotic, anti-inflammatory, and wound healing activity comprising between 0.1 and 10.0% of a dry extract of *Matricaria recutita*, between 0.1 and 10.0% of a dry extract of *Psidium guajava* L. and between 0.1 and 10.0% of a dry extract of *Plantago major* L.

2. The medicinal composition according to claim 1, further comprising between 1.0 and 20.0% of a dry extract of *Casearia sylvestris* SW is added.

3. The medicinal composition according to claim 1, wherein the composition is impregnated in a microbial cellulose biofilm.

4. The medicinal composition according to claim 1, wherein said composition is in liquid form and further comprises between 0.01% and 5.0% of vitamin C, between 0.5% and 3.0% of a wetting agent, between 0.1% and 1% of an antioxidant.

5. The medicinal composition according to claim 4, further comprising between 1.0% and 10.0% of a lyophilized extract of *Casearia sylvestris* SW.

6. The medicinal composition according to claim 4, wherein the composition a pH of approximately 6.0.

7. The medicinal composition according to claim 1, wherein said composition is in solid form and further comprises between 60.0% and 96.0% of a hardness agent.

8. The medicinal composition according to claim 7, further comprising between 1.0% and 10.0% of a lyophilized extract of *Casearia sylvestris* SW.

9. The medicinal composition according to claim 1, wherein each of the dry extracts are in the form of a lyophilized extract.

\* \* \* \* \*